United States Patent [19]

Hall

[11] Patent Number: 4,516,938

[45] Date of Patent: May 14, 1985

[54] BONDABLE LINGUAL RETAINER

[75] Inventor: Arthur B. Hall, LaPorte, Ind.

[73] Assignee: TP Laboratories, Inc., Westville, Ind.

[21] Appl. No.: 575,656

[22] Filed: Jan. 31, 1984

[51] Int. Cl.³ ............................................... A61C 5/00
[52] U.S. Cl. ...................................... 433/215; 433/9; 433/180
[58] Field of Search ............................ 433/9, 180, 215

[56] References Cited

U.S. PATENT DOCUMENTS

| | | | |
|---|---|---|---|
| 4,068,379 | 1/1978 | Miller et al. | 433/9 |
| 4,360,342 | 11/1982 | Salvo | 433/9 |
| 4,433,960 | 2/1984 | Garito et al. | 433/9 |

OTHER PUBLICATIONS

"The Bondable Twin Lower 3-3 Retaining Arch" by Jacob Weisser Jo. of Clin. Orth. 8-1978, pp. 557-560.
TP Laboratories, Inc., Catalog 906, 1981, pp. 11 and 12.

Primary Examiner—John J. Wilson
Attorney, Agent, or Firm—Lee, Smith & Zickert

[57] ABSTRACT

A dental bondable lingual retainer including a plurality of bonding pads or bases interconnected by bar members or links and a method of making same, wherein the retainer is made from a sheet of fused metal foil and mesh, and the connecting bar members or links have the mesh filled with a suitable material for enhancing the strength of the bar members or closed by attaching a foil to the mesh side.

11 Claims, 8 Drawing Figures

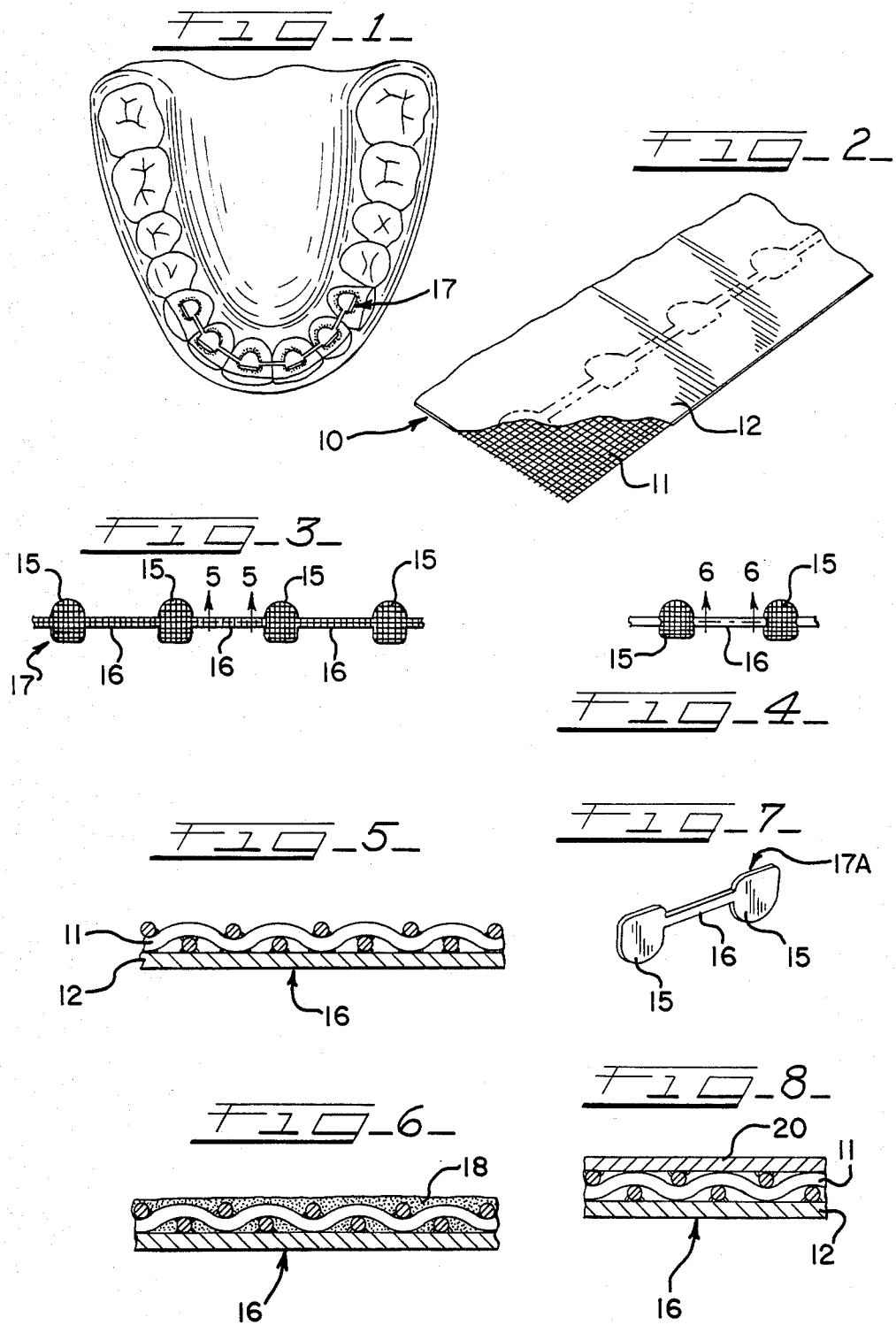

BONDABLE LINGUAL RETAINER

DESCRIPTION

This invention relates in general to a dental bondable lingual retainer for use in the dental treatment of patients, and more particularly to a retainer made from a fused sheet of metal foil and mesh which includes a plurality of bonding pads and interconnecting bars and the mesh of the interconnecting bars is filled with a suitable material to enhance the strength of the bars.

Heretofore, it has been well known to fabricate preformed or custom-made bondable lingual retainers from round or rectangular solid or twisted wire and to bond the ends of the wire to adjacent teeth. It has also been known to attach fused metal foil and mesh pads or etched pads to wire where the pads are then to be bonded to teeth. It has also been known to make retainers from various metals including stainless steel, gold and brass. Further, it has been known to make such retainers where the pads and interconnecting bar members are stamped in one piece from a sheet of stainless steel, and having open mesh welded to the pad areas for facilitating the bonding of the retainer to teeth. Where the mesh material is secured to the pad areas by welding, some open areas of the mesh are closed by the welds, thereby reducing the bondability with teeth. Where wire is secured to fused metal mesh pads, the overall thickness of the retainer is increased, which can result in irritations to the mouth.

The present invention overcomes the problems heretofore encountered in bondable retainers in that a low profile of the retainer is obtained, while maintaining the bondability of the pad areas. The retainer of the present invention is made from a sheet of fused metal foil and open mesh by stamping the form of the retainer from the sheet and thereafter filling the mesh of the interconnecting bars with a material to enhance the bar strength or to attach a foil to the mesh side. One form of material used is stainless steel where both the mesh and the foil are of stainless steel, and one form of filler for the interconnecting bars is solder which is applied to the interconnecting bar following the stamping operation. The soldered interconnecting bar not only enhances the strength of the bar but also permits the bar to be easily bendable and flexible so that it can readily absorb the movement of adjacent teeth during mastication without causing any fracturing of the bonds between the pads and the teeth. The retainer of the invention may be made with any number of bondable pads and interconnecting bars.

It is therefore an object of the present invention to provide a new and improved dental bondable lingual retainer that overcomes the problems of heretofore known retainers and which can be easily and economically made.

A further object of this invention is in the provision of a new and improved dental bondable lingual retainer made from a sheet of fused metal foil and mesh to define a plurality of spaced bonding pads interconnected by bar members and filling of the bar members with a suitable material to enhance their strength and prevent this accumulation of plaque and other debris, while permitting them to have the desired flexibility for ease of mounting and absorption of movement between adjacent teeth without fracturing the bonds between the bonding bases and the teeth.

A further object of this invention is in the provision of a new and improved dental bondable lingual retainer made from a sheet of fused metal foil and mesh to define a plurality of spaced bonding pads interconnected by bar members and attaching a foil to the mesh side of the bar members to enhance their strength and close the mesh to avoid the accumulation of plaque and other debris.

Other objects, features and advantages of the invention will be apparent from the following detailed disclosure, taken in conjunction with the accompanying sheet of drawings, wherein like reference numerals refer to like parts, in which:

FIG. 1 is a bottom plan view of a model of an upper arch having one form of the lingual retainer of the invention mounted in place on the anterior teeth;

FIG. 2 is a perspective view of a sheet of fused metal foil and mesh with a part of the metal foil broken away to show the mesh and illustrating an outline of a retainer to show how the retainer may be stamped from the sheet of fused foil and mesh;

FIG. 3 is a rear elevational view showing the mesh side of the stamped material;

FIG. 4 is a view similar to FIG. 3 but showing the mesh of the interconnecting bar members filled with the material such as solder;

FIG. 5 is an enlarged sectional view taken along line 5—5 of FIG. 3 illustrating the form of the fused metal foil and mesh prior to filling the mesh;

FIG. 6 is an enlarged sectional view taken through the interconnecting bar substantially along line 6—6 of FIG. 4 and showing how the solder or suitable material fills the mesh material in the interconnecting bars;

FIG. 7 is a foil side perspective view of a form of the retainer of the invention which would only include a pair of pads connected by a single interconnecting bar and which would serve as a central-to-central retainer; and FIG. 8 is a view similar to FIG. 5 but showing another embodiment where the mesh side of the connecting bars has a foil layer attached.

The bondable retainer of the invention is preferably made from a sheet of fused stainless steel foil and mesh which has been used for many years for making bondable mesh pads. While this fused foil and mesh material is preferably stainless steel, it should be appreciated it could be made of other suitable metal. A sheet of the fused metal mesh and foil is generally designated by the numeral 10 in FIG. 2 and includes a layer or sheet of open woven mesh 11 and a layer or sheet of foil 12. The two layers are fused together in a well known fashion by the application of heat and pressure which results in each of the contacting areas of the mesh and foil to be bonded or welded together as well as each of the interstices of the mesh to be bonded or welded together so as to essentially form a unitary structure.

The present invention is made by taking a sheet of the fused metal mesh and foil and stamping from it the form of the retainer desired which in one form, as shown in FIG. 3, includes a plurality of bonding pads 15 in spaced apart relation and of a form suitable for application to a tooth and interconnected by bar members 16 of a suitable size which when the structure is completed will provide the desired strength and flexibility between the bonding pads. The retainer shown in FIG. 3 is generally designated by the numeral 17 and following the stamping of the sheet of fused mesh and foil wherein the cross section of the interconnecting bars apepars as illustrated in FIG. 5 the mesh layer is filled with solder 18, as shown in FIG. 6, to enhance the strength of the interconnecting bars. While solder is preferred as the material for filling the open mesh in the interconnecting bars, it may be appreciated that other suitable materials may be used. Thus, the solder is filled in the mesh material through the length of the interconnecting bars and up to the bonding pads 15 where the mesh is left in open form, as shown in FIG. 4, so that the bonding pads will be suitable for bonding to a tooth with a suitable bonding material. Filling the open mesh of the connecting bars 16 with soldering enhances the strength of the interconnecting bars but also permits the bars to have sufficient flexibility to absorb movement between adjacent teeth during mastication without fracturing the bonds at the bonding pads. Further, the mesh is closed to avoid the accumulation of plaque and other debris.

While it may be appreciated that any number of bonding pads may be provided, a central-to-central lingual retainer 17A is illustrated in FIG. 7, which includes a pair of bonding pads 15 interconnected by a bar member 16 which would be bonded to the adjacent centrals in a patient's mouth.

Another embodiment is shown in FIG. 8 where a foil 20 is attached to the mesh side of the connecting bar by welding and/or soldering to close the mesh and enhance the strength of the bar.

From the foregoing, it will be appreciated that the bondable lingual retainer of the present invention and the method of making the retainer provides an improved retainer of low profile that overcomes the problems of heretofore known retainers and which can be easily mounted by an orthodontist so as to efficiently perform the retaining function desired.

It will be understood that modifications and variations may be effected without departing from the scope of the novel concepts of the present invention, but it is understood that this application is to be limited only by the scope of the appended claims.

I claim:

1. A dental bondable lingual retainer comprising, a plurality of spaced bonding pads each of which is bondable to a tooth, and a bar interconnecting said adjacent pads, said bonding pads and bar being integrally formed from a laminated sheet consisting of a layer of metal foil fused to a layer of metal mesh, and means for filling and closing the mesh of said bar to enhance the strength of the bar.

2. The retainer defined in claim 1, wherein said filling and closing means is solder filling the mesh.

3. The retainer defined in claim 2, wherein said metal foil and mesh are stainless steel.

4. The retainer defined in claim 1, which includes a pair of pads interconnected by a bar.

5. The retainer defined in claim 1, which includes more than a pair of pads with a bar interconnecting each adjacent pair, and means filling the mesh area of each bar.

6. The retainer defined in claim 1, wherein said filling and closing means includes a sheet of metal foil attached to the mesh side of the bar.

7. The retainer defined in claim 1, wherein said bonding pads are generally rectangular.

8. A method of making a dental lingual retainer from a sheet of fused metal foil and mesh which comprises the steps of stamping the sheet to form a plurality of spaced bonding pads interconnected by a bar, and filling and closing the mesh of the bar to enhance the strength of the bar and prevent the entry of plaque and other debris.

9. The method of claim 8, wherein the step of filling and closing the mesh includes filling the mesh with solder.

10. The method of claim 8, wherein the sheet of fused metal foil and mesh is stainless steel.

11. The method of claim 8, wherein the step of filling and closing the mesh includes attaching thereto a sheet of metal foil.

* * * * *